(12) United States Patent
Chen et al.

(10) Patent No.: US 10,413,449 B2
(45) Date of Patent: Sep. 17, 2019

(54) OXYGEN-GENERATING WOUND DRESSING

(71) Applicant: BenQ Materials Corporation, Taoyuan (TW)

(72) Inventors: Yu-Hong Chen, Taoyuan (TW); Shih-Wei Chao, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 445 days.

(21) Appl. No.: 15/397,626

(22) Filed: Jan. 3, 2017

(65) Prior Publication Data

US 2017/0319394 A1    Nov. 9, 2017

(30) Foreign Application Priority Data

May 3, 2016 (TW) .............................. 105206323 A

(51) Int. Cl.
*A61F 13/02* (2006.01)
*A61F 13/00* (2006.01)

(52) U.S. Cl.
CPC .... *A61F 13/0216* (2013.01); *A61F 13/00068* (2013.01); *A61F 2013/0017* (2013.01)

(58) Field of Classification Search
CPC .. A61M 1/0088; A61M 1/009; A61M 1/0001; A61M 1/0058; A61M 1/0023; A61M 1/0049; A61M 35/00; A61M 27/00; A61M 1/0031; A61M 1/0084; A61F 13/0216; A61F 13/00042; A61F 13/00051; A61F 13/00068; A61F 13/0203; A61F 13/00063; A61F 13/023; A61L 15/60; A61L 15/425; A61L 15/18; A61L 15/26; A61L 15/46; A61L 15/58; A61L 15/44
See application file for complete search history.

(56) References Cited

U.S. PATENT DOCUMENTS

| | | | | |
|---|---|---|---|---|
| 3,286,954 A | * | 11/1966 | Swet ..................... | B64G 1/46 149/36 |
| 3,917,461 A | * | 11/1975 | Kuhl ..................... | B01J 7/02 422/614 |
| 5,578,022 A | * | 11/1996 | Scherson ............ | A61F 13/00068 604/304 |
| 5,788,682 A | * | 8/1998 | Maget ................. | A61F 13/00063 604/290 |

(Continued)

*Primary Examiner* — Manuel A Mendez

(57) ABSTRACT

An oxygen-generating wound dressing is provided. The oxygen-generating wound dressing comprises a housing and a wound contacting layer. The interior of the housing comprises a barrier member to divide the housing into a reactant receptacle and a wound contacting layer receptacle. The reactant receptacle of the housing further comprises a first reactant receptacle, a second reactant receptacle, a check valve disposed between the first reactant receptacle and the second reactant receptacle, a flow regulating device disposed on the second reactant receptacle and a gas deliver tube for fluidly communicating the first reactant receptacle and the wound contacting layer receptacle. The entrance speed of the second reactant into the first reactant receptacle can be controlled by the flow regulating device. The oxygen partial pressure can be maintained preferably and the wound healing can be improved by using the oxygen-generating wound dressing of the present invention.

11 Claims, 2 Drawing Sheets

(56) References Cited

U.S. PATENT DOCUMENTS

| | | | |
|---|---|---|---|
| 7,429,252 B2* | 9/2008 | Sarangapani | A61F 13/00068 602/2 |
| 9,283,131 B2* | 3/2016 | Belson | A61G 10/04 |
| 2009/0259171 A1* | 10/2009 | Joshi | A61K 9/0021 604/24 |
| 2011/0071426 A1* | 3/2011 | Marasco | A61M 1/0084 600/562 |

* cited by examiner

OXYGEN-GENERATING WOUND DRESSING

This application claims the benefit of TW application No. 105206323, filed on May 3, 2016, and the entirety of which is incorporated by reference herein.

BACKGROUND OF THE INVENTION

Field of the Invention

The present invention relates to a wound dressing and particularly relates to an oxygen-generating wound dressing which maintains the wound oxygen partial pressure for facilitating the wound healing.

Description of the Related Art

In the wound healing process, the fibroblast proliferation, angiogenesis, collagen synthesis and reepithelialization are important factors. Soon after injury caused by accident or surgery, undifferentiated mesenchymal cells are transformed to migratory fibroblasts, which migrate into and across the injured wound. It is known that fibroblasts are aerobic in nature. Fibroblasts are stimulated to produce collagen to facilitate the wound healing. The animal studies demonstrate that the rates of collagen synthesis will be increased under hyperoxic conditions. On the other hand, angiogenesis appears to be subject to a gradient of hypoxic tissue stimulation, and new capillaries are prone to extend toward the direction of low oxygen concentration. Epithelialization is also known to be related to the partial pressure of oxygen, wherein the epithelial cells can be proliferated in higher rates under hyperoxic conditions than proliferated under hypoxic conditions.

Several components are involved in the wound healing and sufficient oxygen supply is especially necessary for generating various growth factors and collagen to facilitate the process of wound healing. When the oxygen partial pressure of the wound tissue is too low, the cell function for wound healing will be slowed down or even not be carried out. In accordance with the studies, the phagocytosis of leukocyte is initiated when the oxygen partial pressure of the tissue is greater than 30 mm-Hg; the collagen for tissue healing is synthesized when the oxygen partial pressure of the tissue is greater than 30 mm-Hg; the osteoblastogenesis of fibroblasts are proceeded when the local oxygen partial pressure of the tissue is greater than 30 mm-Hg. In addition, the wound of the diabetic patient is hard to be healed when the local oxygen partial pressure is less than 40 mm-Hg and no more auxiliary treatment provided.

Hyperoxic conditions not only minimize anaerobic flora by inhibiting the growth thereof but also reduce the concentration of other pathogens as well. The supply of oxygen to healing wound tissue may be derived from three sources: oxygen chemically bound to hemoglobin in whole blood; oxygen dissolved in plasma; and oxygen which diffuses into plasma or tissue from the exterior. For epidermal wounds, all sources of oxygen are important. However, for large wounds, such as ulcers, only the tissue at the edges of the ulcer or at its base are well supplied with blood, and the growing granulation tissue, in the absence of oxygen diffusing from the exterior, must be supplied with oxygen by diffusion from blood vessels and plasma, which is a relatively inefficient process.

An conventional oxygen-generating wound dressing was provided to keep the wound tissue maintaining under the hyperoxic condition wherein the conventional oxygen-generating wound dressing comprises a common form material acted as an oxygen carrier substrate to carry oxygen from an external oxygen source to the wound tissue via the form material or oxygen dissolved in the form material to the wound tissue. However, a gas delivery system connected to the external oxygen source is necessary to input oxygen from the external oxygen source into the foam material, which not only is inconvenient when using, but is easy to cause infection of wound due to improper treatment. Furthermore, although the foam material is good air-permeable, the gas dissolved in the foam material is prone to dissipate due to the changes of the environment conditions, such as temperature change. Therefore, it is trade-off to use the foam material as an oxygen carrier substrate and to keep the concentration of oxygen dissolved in the foam material. Besides, when the foam carrier of a wound dressing contacts the wound to release oxygen, the oxygen partial pressure and the release rate thereof is hard to control to obtain a reliable wound healing effect.

Accordingly, an oxygen-generating wound dressing which can maintain the oxygen partial pressure around the wound area more than 40 mm-Hg, avoid the consummation of the oxygen-generating reactants within the oxygen-generating wound dressing during storage, and prevent the injury wound from being irritated by the oxygen-generating reactants or the oxygen-generating end products.

SUMMARY OF THE INVENTION

Accordingly, the present invention is to provide an oxygen-generating wound dressing which can maintain the oxygen partial pressure around the wound area for effectively enhancing the healing of the wound. Furthermore, the oxygen-generating reactants are stored in different receptacles to avoid the oxygen-generating reactants reacting during the shelf life.

The present invention provides an oxygen-generating wound dressing comprising a housing, and a wound contacting layer. The housing of the present oxygen-generating wound dressing comprises a barrier member to divide the housing into a reactant receptacle and a wound contacting layer receptacle. The reactant receptacle comprises a first reactant receptacle, a second reactant receptacle, a check valve, a flow regulating device and a gas delivery tube. The first reactant receptacle is adjacent to the barrier member and used to accommodate a first reactant. The second reactant receptacle is away from the barrier member and used to accommodate a second reactant. The check valve is disposed between the first reactant receptacle and the second reactant receptacle. The flow regulating device is disposed above the second reactant receptacle. The gas delivery tube is fluidly communicated the first reactant receptacle and the wound contacting layer receptacle. The wound contacting layer is housed in the wound contacting layer receptacle for contacting the wound. When the flow regulating device works, the check valve is opened to regulate the flow rate of the second reactant passing through the check valve into the first reactant receptacle.

According to an embodiment of the present invention, the gas delivery tube further comprises a pressure regulating valve.

According to an embodiment of the present invention, the gas delivery tube further comprises a moisture-gas barrier film.

According to an embodiment of the present invention, the gas delivery tube further comprises a filter.

According to an embodiment of the present invention, the barrier member comprises a barrier layer or a moisture-gas barrier film.

According to an embodiment of the present invention, the flow regulating device comprises a press lever.

According to an embodiment of the present invention, the check valve comprises a duckbill check valve.

According to an embodiment of the present invention, the wound contacting layer comprises a manifold structure.

According to an embodiment of the present invention, the wound contacting layer comprises polyurethanes, polyolefins, vinyl acetates, polysiloxanes, fluoro polysiloxanes, fluoro elastomers, styrene, butadiene or thermoplastic elastomers or the likes.

According to an embodiment of the present invention, the housing further comprises a relief valve adjacent to the wound contacting layer receptacle.

According to an embodiment of the present invention, the housing further comprises a buffer layer disposed at the periphery of the housing.

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. The above and other aspects and advantages of the present invention will become apparent from the following detailed description of the present invention taken in conjunction with the drawings.

DETAILED DESCRIPTION OF THE INVENTION

Figure 1:
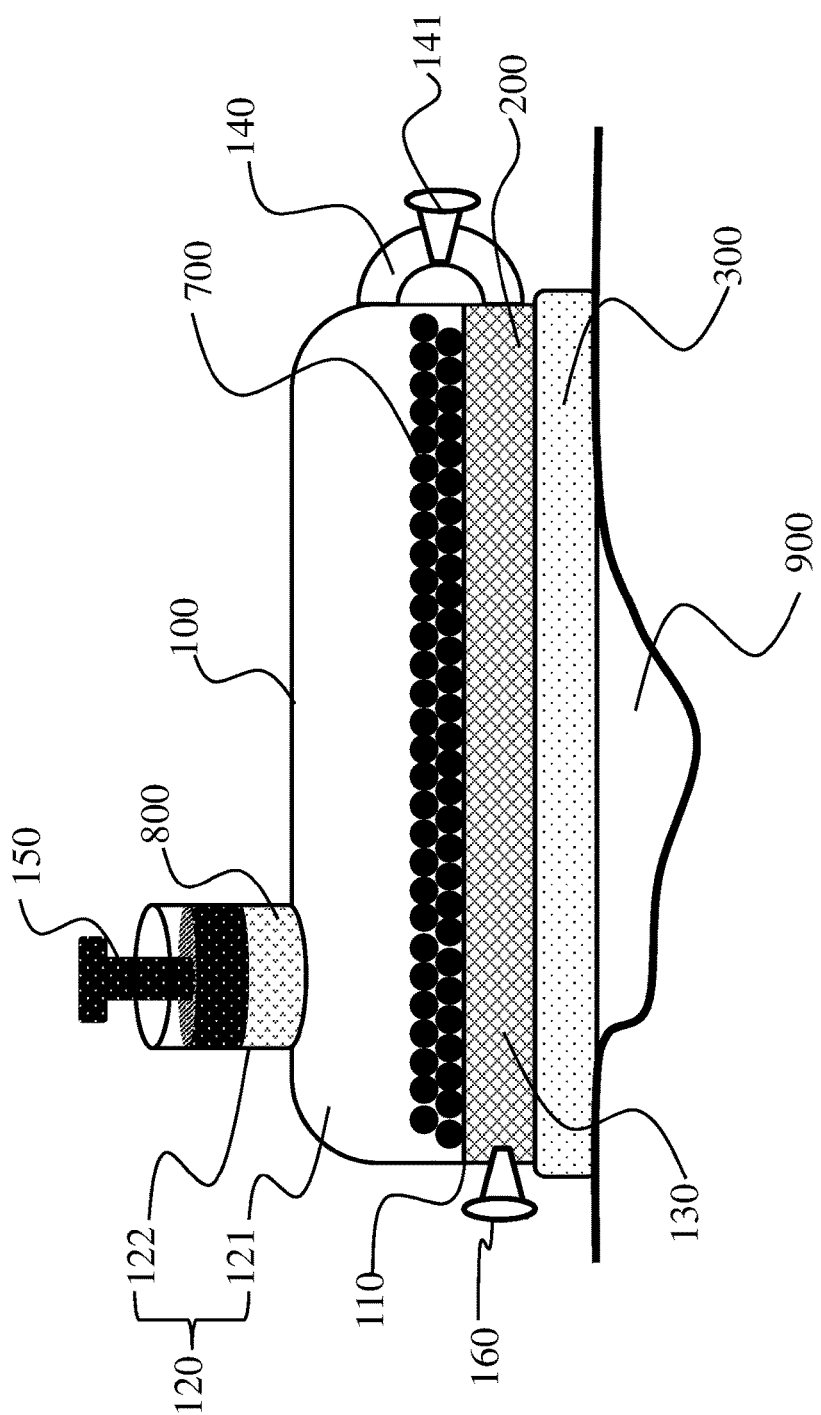
FIG. 1 shows a schematic side view of the oxygen-generating wound dressing of one embodiment of the present invention.

Referring now to the drawings to illustrate the embodiments of the present oxygen-generating wound dressing. In the following embodiments of the present invention, the like elements refer to like symbols in the figures. The following description will introduce the embodiment of the above-described oxygen-generating wound dressing. For being better understood the embodiments of the present invention, a detailed description thereof is provided. However, well-known functions or constructions may not be described in detail for brevity and/or clarity. The drawings are not necessarily to scale, emphasis instead being placed upon illustrating the principles of the invention rather than to limit and restrict of the scope of the present invention defined in the appended claim.

The advantages and features of the present invention will become better understood with reference to the following more detailed description and claims taken in conjunction with the accompanying drawings. It should be understood that the exemplary embodiments of the present invention described below may be modified in many different ways without departing from the inventive principles disclosed herein, and the scope of the present invention is therefore not limited to these particular embodiments. Rather, these embodiments are provided so that this disclosure will be thorough and complete, and will fully convey the concept of the invention to those skilled in the art by way of example and not of limitation. In the drawings, the thickness of layers, films, and regions are exaggerated for clarity. The present invention is only defined by the appended claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal senseless expressly so defined herein.

Referring to FIG. 1 shows a schematic side view of the oxygen-generating wound dressing of one embodiment of the present invention. As shown in FIG. 1, the oxygen-generating wound dressing of the present invention comprises a housing 100 and a wound contacting layer 200. The housing 100 is used for maintaining a sealed environment of the wound area and maintain the oxygen partial pressure of the wound area 900. Preferably, the housing 100 is a rigid body. The housing 100 comprises a barrier member 110 dividing the internal space of the housing 100 into a reactant receptacle 120 and a wound contacting layer receptacle 130. The periphery of the opening of the housing 100 can optionally comprises an adhesive layer, such as an acrylate adhesive layer, for keeping the oxygen-generating wound dressing be adhered onto the skin around the wound. The barrier member 110 is used to divide the housing 100 into a reactant receptacle 120 and a wound contacting layer receptacle 130. Considering the barrier member has to bear the reactants, prevent the reactants from diffusing or permeating into the wound contacting layer receptacle 130, and prevent the generated oxygen from diffusing into the reactant receptacle 120, the barrier member 110 preferably is a barrier plate, a moisture-gas barrier film or the combination thereof.

The wound contacting layer 200 is accommodated in the wound contacting layer receptacle 130. According to one embodiment of the present invention, the wound contacting layer 200 has a manifold structure. The manifold structure means a structure disposed for applying or delivering the fluid to the tissue or removing the fluid from the tissue. The wound contacting layer 200 comprises a plurality of the fluid channels for providing fluids to the tissue and removing fluids from the tissue. The channels are intercommunicated with each other. The wound contacting layer 200 is made of bio-acceptable materials, which is disposed onto the wound tissue to distribute the oxygen thereto. The examples of the materials used as the wound contacting layer 200 include, without limitation, materials that have structural elements arranged to form open channels, such as honeycomb foam, open-cell foam, porous tissue collections, and liquids, gels, and cured foams with open channels. In one embodiment of the present invention, the wound contact layer 200 is a manifold structure made of porous foam, which comprises a plurality of interconnected cells or pores that act as open channels. The porous foam may be an open-cell foam or a reticulated foam consisted of polyurethane, or an open-cell flexible foam consisted of polymer, such as polyolefin, ethylene vinyl acetate, polysiloxane, fluoro polysiloxane, fluoro elastomer, styrene, butadiene or thermoplastic elastomer.

The reactant receptacle 120 of the housing 100 comprises a first reactant receptacle 121 and a second reactant receptacle 122. The first reactant receptacle 121 is adjacent to the barrier member 110 and used to accommodate a first reactant 700, and the second reactant receptacle 122 is away from the barrier member 110 to accommodate a second reactant. Furthermore, a check valve is disposed between the first reactant receptacle 121 and the second reactant receptacle 122 (not shown) to prevent the oxygen generated in the first reactant receptacle 121 from diffusing into the second reactant receptacle 122. In one preferred embodiment of the present invention, the check valve (not shown) is a duckbill check valve, and preferably, the check valve is a rubber duckbill check valve.

The second reactant receptacle 122 comprises a flow regulating device 150 disposed above the second reactant receptacle 122 for regulating the flow rate of the second reactant 800 passing through the check valve (not shown) into the first reactant receptacle 121. When the flow regulating device 150 works, the check valve (not shown) is opened and the second reactant 800 can flow into the first reactant receptacle 121 via the check valve (not shown) and react with the first reactant 700 in the first reactant receptacle 121 to generate oxygen. In one preferred embodiment of the present invention, the flow regulating device 150 is a press lever. By forcing the press lever to apply a pressure to the second reactant receptacle 122, the second reactant 800 will enter into the first reactant receptacle 121 through the duckbill valve opened due to the pressure. The oxygen generated by the reaction of the second reactant 800 and the first reactant 700 can be delivered into the wound contacting layer 200 by the gas delivery tube 140 which fluidly communicates the first reactant receptacle 121 and the wound contacting layer receptacle 130. The gas delivered into the wound contacting layer 200 can be evenly distributed to the wound area 900. When the reaction is over or the oxygen partial pressure around the wound area 900 is insufficient, the flow regulating device 150 can work again to accelerate the reaction of the first reactant 700 and the second reactant 800 to generate oxygen to maintain the oxygen partial pressure around the wound area 900.

For regulating the oxygen partial pressure around the wound area 900, the gas delivery tube 140 can further comprise a pressure regulating valve 141 to regulate the oxygen delivery rate to maintain a suitable pressure around the wound area 900. When the oxygen partial pressure of the wound area 900 is insufficient, the pressure regulating valve 141 is opened to allow the oxygen generated in the first reactant receptacle 121 to diffuse into the wound contacting layer receptacle 130. On the contrary, when the oxygen partial pressure of the wound area 900 is sufficient, the pressure regulating valve 141 is closed to avoid the oxygen generated in the first reactant receptacle 121 to diffuse into the wound area 900. In one preferred embodiment of the present invention, the gas delivery tube 140 can optionally further comprises a gas permeable and moisture barrier film or a filter to prevent any unreacted reactant or harmful substance to the wound from being delivered to the wound area together with the oxygen through the gas delivery tube 140.

Figure 2:
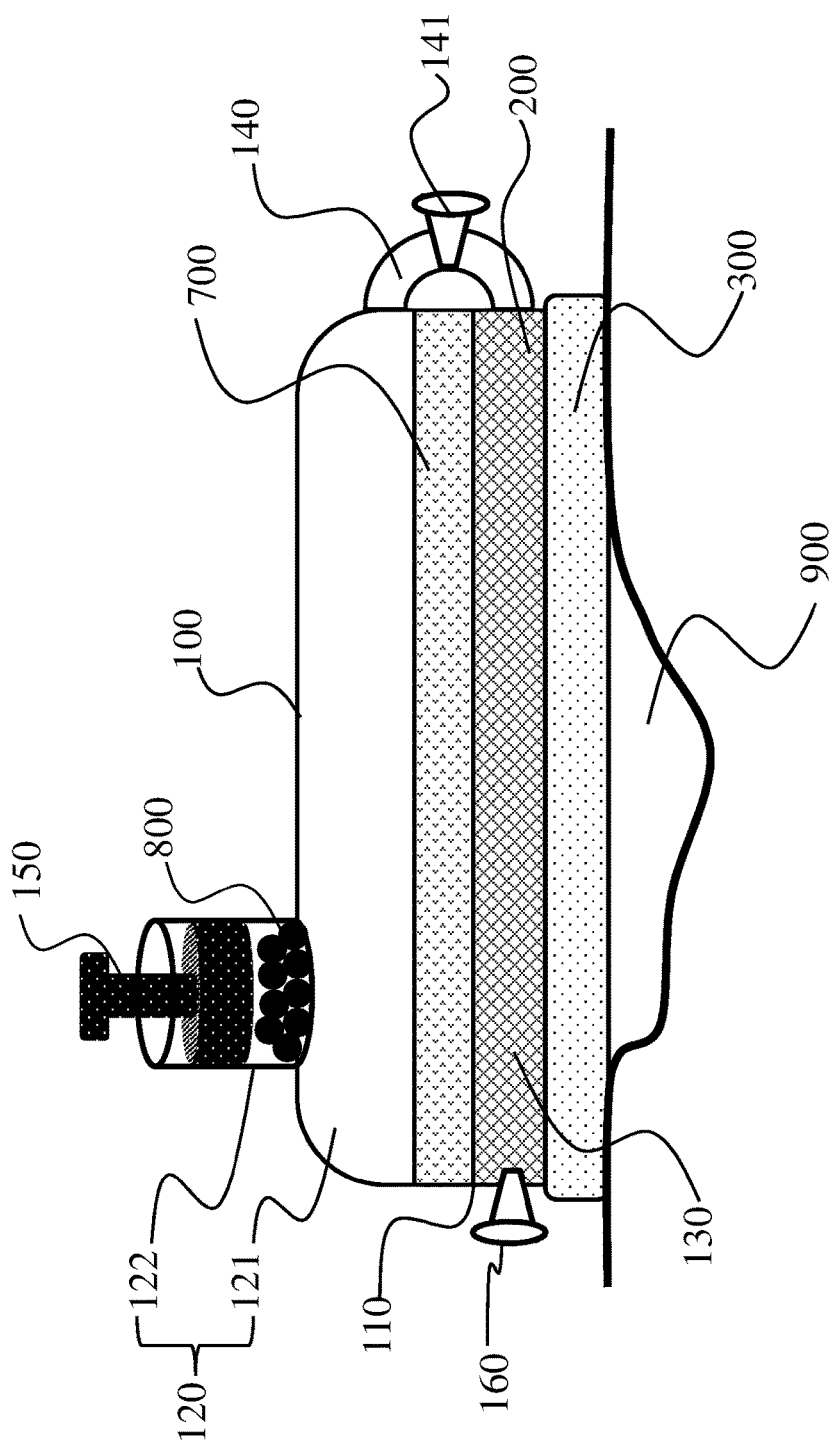
FIG. 2 shows a schematic side view of the oxygen-generating wound dressing of another embodiment of the present invention.

The first reactant 700 can be an oxygen-generating precursor, and the second reactant 800 can be an oxygen-generating catalyst. The first reactant 700 and the second reactant 800 can react to generate oxygen. In one preferred embodiment of the present invention, the first reactant 700 is a solid oxygen-generating precursor including but not limited to calcium peroxide, lithium peroxide, sodium peroxide, urea peroxide, potassium superoxide, sodium peroxyhydrate and the likes. The second reactant 800 is a liquid catalyst including but not limited to water or metal ions-containing aqueous solutions, such as manganese ions-containing aqueous solution or iron ions-containing aqueous solution, as shown in FIG. 1. In another embodiment of the present invention, the first reactant 700 is a liquid oxygen-generating precursor including but not limited to hydrogen peroxide, and the second reactant 800 is a solid catalyst including but not limited to manganese dioxide, as shown in FIG. 2.

In one preferred embodiment of the present invention, the housing 100 can optionally further comprise a relief valve 160 adjacent to the wound contacting layer receptacle 130 to release excess oxygen to regulate the oxygen partial pressure around the wound area 900.

For the wear comfort, in one preferred embodiment of the present invention, the housing 100 can optionally further comprise a buffer layer 300. The buffer layer 300 is disposed at the periphery of the housing 100 for improving the wear comfort when using the oxygen-generating wound dressing of the present invention, as shown in FIGS. 1 and 2. The buffer layer 300 can be made of closed-cell foam, rubber or latex with a proper thickness or an air-cushion structure. The buffer layer 300 can optionally further comprise an adhesive layer, such as a pressure sensitive acrylates adhesive, to adhere the oxygen-generating wound dressing onto the skin around wound area 900 to enhance the fixing of the oxygen-generating wound dressing.

When using the oxygen-generating wound dressing of the present invention, the second reactant 800 accommodated in the second reactant receptacle 122 is first released into the first reactant receptacle 121 via the check valve (not shown) to react with the first reactant 700 to generate oxygen by initiating the flow regulating device 150. Next, the generated oxygen is regulated by the pressure regulating valve 141 of the gas delivery tube 140 to diffuse into the wound contacting layer receptacle 130 in order to evenly distribute the oxygen to the wound area 900 via the wound contacting layer 200 and maintain the oxygen partial pressure around the wound 900 area. When the reaction is over, the flow regulating device 150 is initiated again to release the second reactant 800 into the first reactant receptacle 121 via the check valve (not shown) to continue the oxygen-generating reaction. When the partial pressure of the wound area 900 is too high, the partial pressure around the wound area 900 can be regulated by the pressure regulating valve 141 or the relief valve 160. Therefore, the oxygen generating wound dressing of the present invention can advantageously maintain the oxygen partial pressure around the wound area 900 to facilitate the wound healing.

The present invention provides the following advantages:

1. The advantage of the oxygen-generating wound dressing of this present invention over the conventional oxygen-generating wound dressing with oxygen dissolved therein is to prolong the shelf life by storing oxygen-generating reactants in different receptacles.

2. Because the oxygen-generating reactants are separately stored in different receptacles away from the wound area, the wound area will not suffer from any irritation caused by the reactants. Furthermore, the air permeable water barrier layer or filter disposed in the gas delivery tube can prevent the wound area from contacting the unreacted reactants.

3. The construction of the housing is to provide a better way to maintain the oxygen partial pressure of the wound area, the oxygen-generating wound dressing of the present invention can regulate the oxygen content around the wound area via the pressure regulating valve of the gas delivery tube and the relief valve of the housing to control the oxygen partial pressure for wound healing.

4. The housing and the reactants can be packaged after sterilization. Therefore, the interior of the present oxygen-generating wound dressing is sterilized and no external pressure source is needed, the infection caused by the known oxygen-generating wound dressing can be reduced.

Accordingly, the oxygen-generating wound dressing of the present invention is advantage of easy storage, maintaining the oxygen partial pressure of the wound area and reducing the risk of wound infection to facilitate the wound healing.

While the invention has been described by way of example(s) and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An oxygen-generating wound dressing comprising:
   a housing, comprising a barrier member to divide the housing into a reactant receptacle and a wound contacting layer receptacle, wherein the reactant receptacle further comprising:
   a first reactant receptacle adjacent to the barrier member for accommodating a first reactant;
   a second reactant receptacle away from the barrier member for receiving a second reactant;
   a check valve disposed between the first reactant receptacle and the second reactant receptacle;
   a flow regulating device disposed above the second reactant receptacle, wherein the check valve is opened to regulate the flow rate of the second reactant passing through the check valve into the first reactant receptacle when the flow regulating device works; and
   a gas delivery tube fluidly communicated the first reactant receptacle and the wound contacting layer receptacle; and
   a wound contacting layer, housed in the wound contacting layer receptacle for contacting the wound.

2. The oxygen-generating wound dressing as claimed in claim 1, wherein the gas delivery tube further comprises a pressure regulating valve.

3. The oxygen-generating wound dressing as claimed in claim 1, wherein the gas delivery tube further comprises an air permeable water barrier layer.

4. The oxygen-generating wound dressing as claimed in claim 1, wherein the gas delivery tube further comprises a filter.

5. The oxygen-generating wound dressing as claimed in claim 1, wherein the barrier member comprises a barrier layer or a moisture-gas barrier film.

6. The oxygen-generating wound dressing as claimed in claim 1, wherein the flow regulating device comprises a press lever.

7. The oxygen-generating wound dressing as claimed in claim 1, wherein the check valve comprises a duckbill check valve.

8. The oxygen-generating wound dressing as claimed in claim 1, wherein the wound contacting layer comprises a manifold structure.

9. The oxygen-generating wound dressing as claimed in claim 1, wherein the wound contacting layer comprises polyurethanes, polyolefins, vinyl acetates, polysiloxanes, fluoro polysiloxanes, fluoro elastomers, styrene, butadiene or thermoplastic elastomers.

10. The oxygen-generating wound dressing as claimed in claim 1, further comprising a relief valve adjacent to the wound contacting layer of the housing.

11. The oxygen-generating wound dressing as claimed in claim 1, further comprising a buffer layer disposed adjacent to the periphery of the housing.

* * * * *